Figure 1:
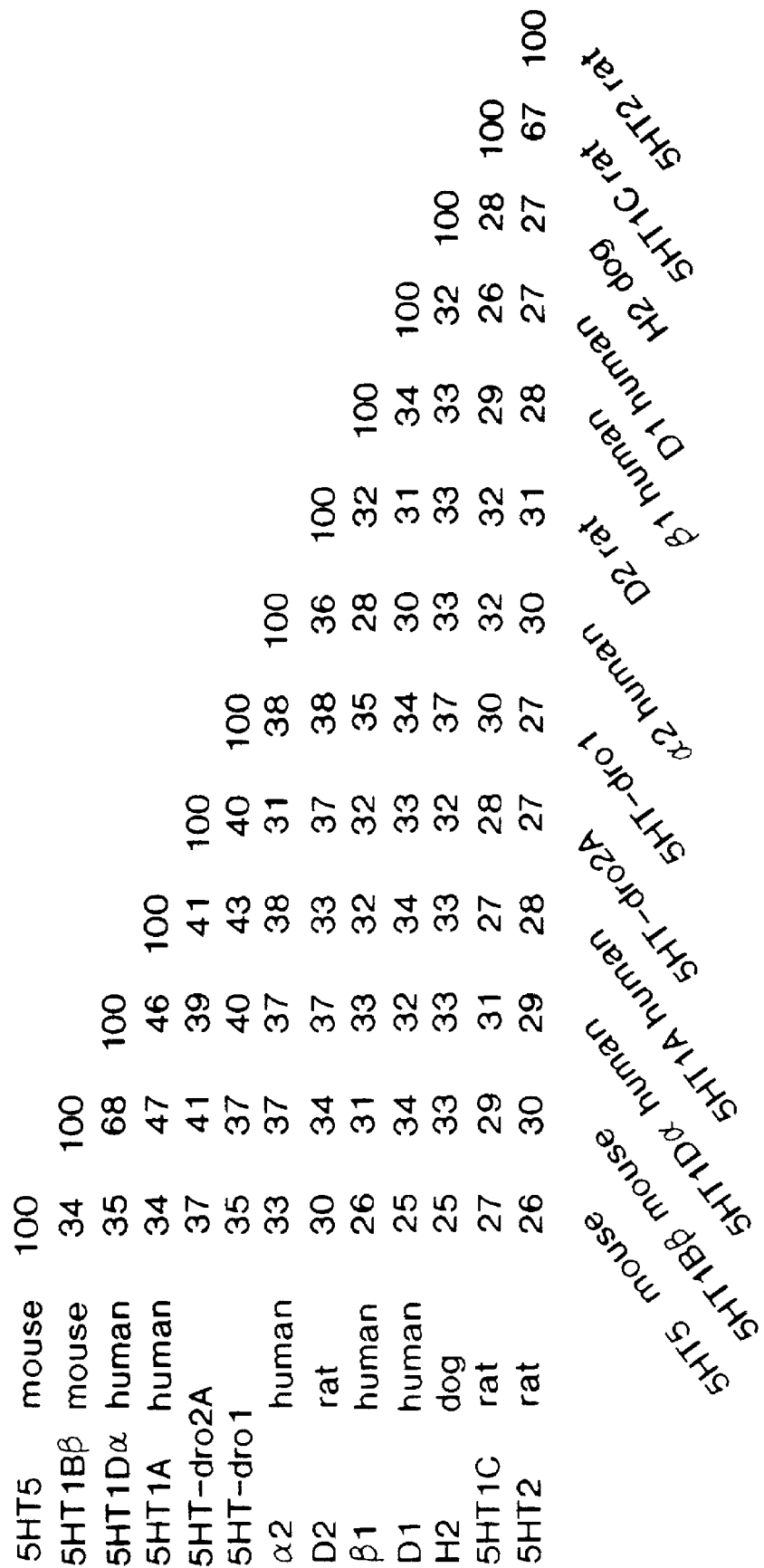

United States Patent [19]
Amlaiky et al.

[11] Patent Number: 5,807,691
[45] Date of Patent: Sep. 15, 1998

[54] POLYPEPTIDES HAVING SEROTONIN RECEPTOR ACTIVITY (5HT5A), NUCLEIC ACIDS CODING FOR THESE POLYPEPTIDES AND USES THEREOF

[75] Inventors: Nourdine Amlaiky; Ursula Boschert; René Hen; Jean-Luc Plassat, all of Strasbourg, France

[73] Assignee: Institut National De La Sante et Da La Recherche Medicale, Paris, France

[21] Appl. No.: 356,405

[22] PCT Filed: Jun. 29, 1993

[86] PCT No.: PCT/FR93/00650

§ 371 Date: Mar. 29, 1995

§ 102(e) Date: Mar. 29, 1995

[87] PCT Pub. No.: WO94/01555

PCT Pub. Date: Jan. 20, 1994

[30] Foreign Application Priority Data

Jul. 1, 1992 [FR] France .................................. 92-08081

[51] Int. Cl.⁶ .......................... C12N 15/00; C07K 14/705
[52] U.S. Cl. ...................... 435/7.21; 536/23.5; 536/24.3; 536/24.31; 536/24.33; 435/6; 435/69.1; 435/320.1; 435/325; 530/350
[58] Field of Search .................................. 536/23.1, 23.5, 536/24.3, 24.31, 24.33; 435/6, 172.3, 69.1, 240.2, 252.34, 7.1, 7.2, 7.21; 514/2, 12

[56] References Cited

U.S. PATENT DOCUMENTS 5,155,218  10/1992  Weinshank et al. ...................... 536/27
5,389,527  2/1995  Beavo et al. ............................ 435/69.1

FOREIGN PATENT DOCUMENTS 4041464  12/1990  Germany .
WO91/17174  5/1991  WIPO .

OTHER PUBLICATIONS

Proc. Natl. Acad. Sci. USA 89(12):5517–21, 1992, McAllister Charlesworth Snodin, Beer Noble et al., Molecular Cloning of a Serotonin Receptor From Human Brain (5HT1E): A Fifth 5HT1–Like Subtype.

Primary Examiner—Marianne P. Allen
Attorney, Agent, or Firm—Seidel, Gonda, Lavorgna & Monaco, PC

[57] ABSTRACT

The present invention concerns novel polypeptides designated 5HT5a having serotonin receptor activity, genetic material permitting their expression, any recombinant cell expressing said polypeptides and uses thereof.

15 Claims, 3 Drawing Sheets

POLYPEPTIDES HAVING SEROTONIN RECEPTOR ACTIVITY (5HT5A), NUCLEIC ACIDS CODING FOR THESE POLYPEPTIDES AND USES THEREOF

The present invention relates to new polypeptides and to the genetic material permitting their expression. More especially, it relates to new polypeptides having serotonin receptor activity.

Serotonin is a neuromodulator capable of inducing and modulating a wide variety of behavioral functions such as sleep, appetite, locomotion, sexual activity and vascular contraction. It is accepted that serotonin activity is mediated by interaction of the compound with receptors, designated serotonin receptors or 5-HT (for 5-hydroxytryptamine) receptors. Molecular biology studies as well as pharmacological studies have revealed the existence of a large number of subtypes of 5-HT receptors. The 5-HT receptors which have been described to date belong either to the family of receptors associated with ion channels (5-HT3 receptors), or to the family of receptors which interact with G proteins and which possess seven transmembrane domains. Moreover, analysis of the amino acid sequences has shown that the 5-HT receptors which interact with G proteins may be subdivided into two distinct groups: 5HT1 receptors, comprising the mammalian subtypes 5HT1A, 5HT1B and 5HT1D, as well as three drosophila 5HT receptors; and 5HT2 receptors comprising the subtypes 5HT2 and 5HT1C.

These receptors are doubtless not the only 5HT receptors which exist, inasmuch as pharmacological studies have revealed other subtypes, such as 5HT4 receptors as well as some receptors related to the subtype 5HT1 ("5HT1 -like" receptors). Furthermore, additional molecular biology studies have also revealed heterogeneities within the subtypes 5HT1 B/1 D.

The present invention is the outcome of the demonstration of new polypeptides having serotonin receptor activity. While belonging to the family of receptors which interact with G proteins, these new polypeptides differ from the serotonin receptors already described (5HT1, 5HT2, 5HT3 and 5HT4) from both a structural standpoint and a pharmacological standpoint. More especially, the invention is the outcome of the isolation and characterization of these new polypeptides, designated 5HT5a, and also of the genetic material permitting their expression or identification.

A first subject of the invention hence lies in polypeptides comprising all or part of the sequence SEQ ID No. 1 or of a derivative of the latter.

For the purposes of the present invention, the term derivative denotes any molecule obtained by modification, of a genetic and/or chemical nature, of the peptide sequence SEQ ID No. 1. Modification of a genetic and/or chemical nature may be understood to mean any mutation, substitution, deletion, addition and/or modification of one or more residues. Such derivatives may be generated for different purposes, such as, in particular, that of increasing the affinity of the peptide for its ligand(s), that of improving its levels of production, that of increasing its resistance to proteases, that of increasing and/or modifying its activity or that of endowing it with new pharmacokinetic and/or biological properties. Among derivatives resulting from an addition, chimeric polypeptides containing an additional heterologous portion attached at one end may, for example, be mentioned. The term derivative also comprises polypeptides homologous with the polypeptide SEQ ID No. 1, originating from other cell sources, and in particular from cells of human origin or of other organisms and possessing an activity of the same type. Such homologous polypeptides may be obtained by hybridization experiments, as described in the examples. In particular, the invention also relates to the peptides of sequence SEQ ID No. 8 corresponding to the human receptor.

Preferably, the polypeptides of the invention are polypeptides possessing the capacity to bind serotonin. Still more preferably, they are polypeptides having serotonin receptor activity. Still according to a preferred embodiment, the polypeptides of the invention are capable of being recognized by antibodies which recognize the complete peptide sequence SEQ ID No. 1.

A particular embodiment of the invention is represented by the polypeptide 5HT5a comprising the whole peptide sequence SEQ ID No. 1 or SEQ ID No. 8. As shown in the examples, this polypeptide may be expressed in different cell types to form a functional serotonin receptor.

The polypeptides of the invention may be obtained by expression of a nucleotide sequence as described below in a cell host, by chemical synthesis on the basis of the sequence SEQ ID No. 1 using techniques known to a person skilled in the art, or by a combination of these techniques.

In what follows, the polypeptides of the invention as defined above are designated 5HT5a polypeptides.

The subject of the present invention is also any nucleotide sequence coding for a 5HT5a polypeptide. More preferably, such a sequence is chosen from:

(a) all or part of the nucleotide sequence SEQ ID No. 1 or of its complementary strand, (b) any sequence hybridizing with a sequence (a) and coding for a polypeptide as defined above, and (c) the sequences derived from the sequences (a) and (b) as a result of the degeneracy of the genetic code.

The different nucleotide sequences of the invention can be of artificial origin or otherwise. They can be genomic, cDNA or RNA sequences, hybrid sequences or synthetic or semi-synthetic sequences. These sequences may be obtained, for example, by screening DNA libraries (cDNA library, genomic DNA library) by means of probes devised on the basis of the sequence SEQ ID No. 1. Such libraries may be prepared from cells of different origins by standard techniques of molecular biology known to a person skilled in the art. The nucleotide sequences of the invention may also be prepared by chemical synthesis, in particular according to the phosphoramidite method, or alternatively by mixed methods including the chemical or enzymatic modification of sequences obtained by screening libraries.

The nucleotide sequences of the invention may be used for the production of 5HT5a polypeptides as defined above. In this case, the portion coding for the said polypeptide is generally placed under the control of signals permitting its expression in a cell host. The choice of these signals (promoters, terminators, and the like) can vary in accordance with the cell host used. To this end, the nucleotide sequences of the invention can form part of a vector, which can be an autonomously replicating or integrative vector. More especially, autonomously replicating vectors may be prepared using sequences which replicate autonomously in the chosen host. As regards integrative vectors, these may be prepared, for example, using sequences homologous with certain regions of the host's genome, permitting integration of the vector by homologous recombination. The cell hosts which are usable for the production of the 5HT5a polypeptides of the invention by the recombinant method are either eukaryotic or prokaryotic hosts. Among suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 and NIH-3T3 cells, and the like, may be mentioned. Among fungi, *Aspergillus ssp.* or *Trichoderma ssp* . may be mentioned more especially. As prokaryotic hosts, it is preferable to use the following bacteria: *E. coli*, Bacillus or Streptomyces.

The nucleotide sequences of the present invention are also usable in the pharmaceutical field, either for the production of antisense sequences which may be used in the context of a gene therapy, or else for the production of probes permitting the detection, by hybridization experiments, of the expression of serotonin receptors in biological samples, and the demonstration of genetic abnormalities (polymorphism, mutations) or of aberrant expressions.

Inhibition of the expression of certain genes by antisense oligonucleotides has proved to be a promising strategy in controlling the activity of a gene. Antisense oligonucleotides are small-sized oligonucleotides complementary to the coding strand of a given gene and, as a result, capable of hybridizing specifically with the transcribed mRNA inhibiting its translation into protein. A subject of the invention is thus antisense oligonucleotides capable of at least partially inhibiting the production of 5HT5a polypeptides as defined above. Such oligonucleotides can consist of all or part of the nucleotide sequences defined above. They are generally sequences or fragments of sequences complementary to sequences coding for peptides of the invention. Such oligonucleotides may be obtained from the sequence SEQ ID No. 1 or SEQ ID No.8, by fragmentation, and the like, or by chemical synthesis.

As stated above, the invention also makes it possible to produce nucleotide probes, synthetic or otherwise, capable of hydriding with the nucleotide sequences defined above which code for 5HT5a polypeptides of the invention, or with the corresponding mRNAs. Such probes may be used in vitro as a diagnostic tool for detecting the expression of a 5HT5a serotonin receptor, or alternatively for demonstrating genetic abnormalities (incorrect splicing, polymorphism, point mutations, and the like). In view of the numerous activities of serotonin, the probes of the invention may thus enable neurological, cardiovascular or psychiatric disorders to be identified as being associated with 5HT5a receptors. These probes may also be used for demonstrating and isolating homologous nucleic acid sequences coding for 5HT5a polypeptides as defined above, from other cell sources and preferably from cells of human origin, as illustrated in the examples. The probes of the invention generally contain at least 10 bases, and they can contain as much as the whole of the sequence SEQ ID No. 1 or SEQ No. 8, or of their complementary strand. Preferably, these probes are labelled prior to their use. For this purpose, different techniques known to a person skilled in the art may be employed (radioactive or enzymatic labelling, and the like). The hybridization conditions under which these probes may be used are mentioned in the general cloning techniques below, as well as in the examples.

Another subject of the invention relates to recombinant cells capable of expressing at their surface a 5HT5a polypeptide as defined above. These cells may be obtained by introducing a nucleotide sequence as defined above, coding for a polypeptide of the invention, and then culturing the said cells under conditions for expression of the said sequence.

The recombinant cells according to the invention can be either eukaryotic or prokaryotic cells. Among suitable eukaryotic cells, animal cells, yeasts or fungi may be mentioned. In particular, as regards yeasts, yeasts of the genus Saccharomyces, Kluyveromyces, Pichia, Schwanniomyces, or Hansenula may be mentioned. As regards animal cells, COS, CHO, C127 and NIH-3T3 cells, and the like, may be mentioned. Among fungi, *Aspergillus ssp.* or *Trichoderma ssp*. may be mentioned more especially. As prokaryotic cells, it is preferable to use the following bacteria: *E. coli*, Bacillus or Streptomyces. The cells thereby obtained may be used to measure the ability of different molecules to behave as a ligand or as a modulator of the activity of the polypeptides of the invention. More especially, they may thus be used in a method for demonstrating and isolating ligands or modulator of the activity of the polypeptides of the invention, and more preferably serotonin agonists and antagonists.

Another subject of the invention hence relates to a method for demonstrating and/or isolating ligands of the 5HT5a polypeptides of the invention, according to which the following steps are carried out:

a molecule or a mixture containing different molecules, which are possibly unidentified, is brought into contact with a recombinant cell as described above, expressing at its surface a polypeptide of the invention, under conditions permitting interaction between the said polypeptide of the invention and the said molecule should the latter possess an affinity for the said polypeptide, and the molecules bound to the said polypeptide of the invention are detected and/or isolated.

In a particular embodiment, this method of the invention is suitable for demonstrating and/or isolating serotonin agonists and antagonists for the 5HT5a polypeptides.

Another subject of the invention relates to a method for demonstrating and/or isolating modulators of the 5HT5a polypeptides of the invention, according to which the following steps are carried out:

a molecule or a mixture containing different molecules, which are possibly unidentified, is brought into contact with a recombinant cell as described above, expressing at its surface a polypeptide of the invention, in the presence of 5HT, under conditions permitting interaction between the said polypeptide of the invention and 5HT, and the molecules capable of modulating the activity of 5HT with respect to he said polypeptide of the invention are detected and/or isolated.

Another subject of the invention relates to the use of a ligand or modulator identified and/or obtained according to the method described above, as a medicinal product. Such ligands or modulators can, in effect, enable certain neurological, cardiovascular or psychiatric disorders associated with 5HT5a receptors to be treated.

The invention also relates to any medicinal product comprising as active principle at least one molecule which acts on a 5HT5a polypeptide of the invention. Preferably, the molecule is a ligand or a modulator identified and/or isolated according to the method described above.

Other advantages of the present invention will become apparent on reading the examples which follow, which are to be considered as illustrative and non-limiting.

LEGEND TO THE FIGURE

SEQ ID No. 1: Nucleotide and peptide sequences of the 5HT5a receptor. The 4-kb cDNA was sequenced on both strands from the EcoRI site to position 1685. The remaining 2,300 nucleotides were not sequenced, except for the 3' end containing the poly(A) tail.

FIG. 1: Peptide sequence percentage homologies between the 5HT5a receptor SEQ ID No. 1 and other receptors of the family of receptors coupled to G proteins. The homologies were calculated on the conserved sequences: the transmembrane domain and its connecting loops.

Figure 2A:
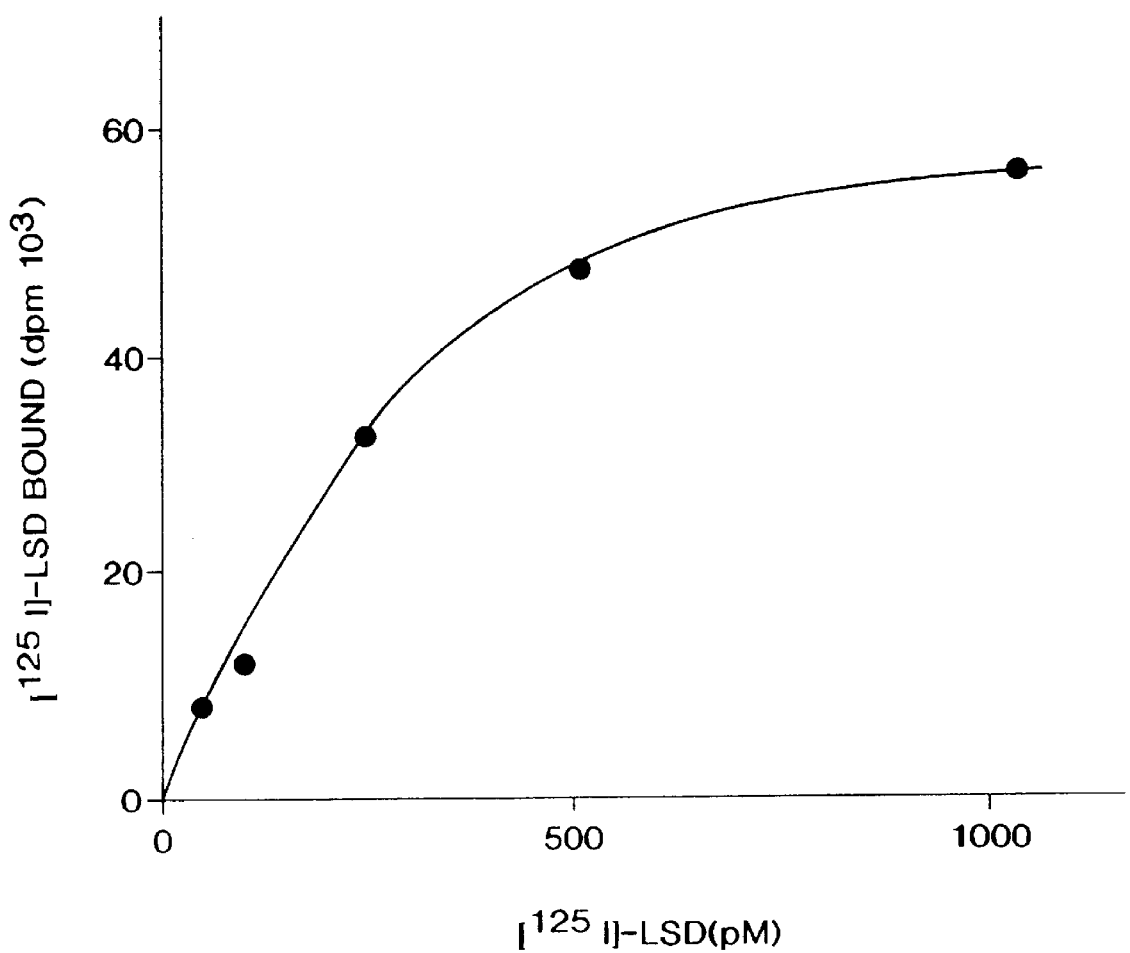
Figure 2B:
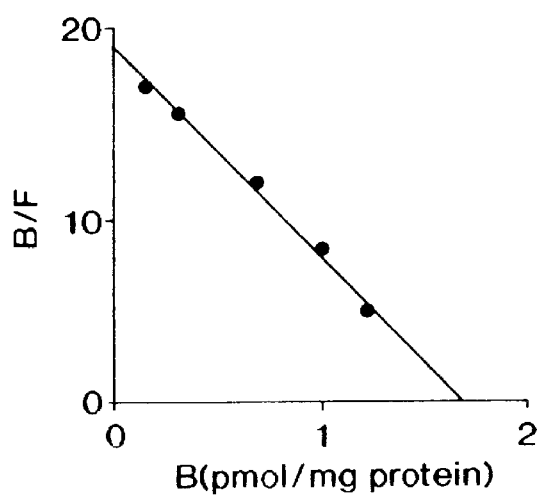

FIG. 2: Saturation curve for [$^{125}$I]-LSD at the membranes of Cos-7 cells expressing the 5HT5a receptor. The membranes were incubated with ligand concentrations ranging from 50 pM to 1.25 nM, with or without 10 μM 5HT. The specific binding is shown. The inset shows the Scatchard analysis of the results.

FIG. 3: Demonstration of homologous sequences: (a) by Northern blotting on poly(A) mRNA (5 μg) of different tissues; (b) by PCR on total RNAs (1 μg) of different tissues.

Table 1: Pharmacological profile of the 5HT5a receptor. The results correspond to experiments on competition for the binding of [$^{125}$I]-LSD, either to the membranes of Cos-7 cells transiently expressing the 5HT5a receptor, or to the membranes of NS4 cells stably expressing the 5HT5a receptor. The $IC_{50}$ values (corresponding to the ligand concentration needed to displace 50% of the bound [$^{125}$I]-LSD) were calculated experimentally and converted to Ki according to the following equation: $Ki=IC_{50}/(1+C/Kd)$, in which C is the [$^{125}$I]-LSD concentration and Kd is the dissociation constant of [$^{125}$I]-LSD (308 pM). The numbers in brackets correspond to the number of independent experiments carried out, each point being produced in triplicate.

General Cloning Techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extractions with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York 1987].

Restriction enzymes were supplied by New England Biolabs (Biolabs), Bethesda Research Laboratories (BRL) or Amersham, and are used according to the suppliers' recommendations.

For ligation, the DNA fragments are separated according to size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling-in of 5' protruding ends is performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides is performed according to the method developed by Taylor et al. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique is performed using a "DNA thermal cycler" (Perkin Elmer Cetus) according to the manufacturer's specifications.

Verification of the nucleotide sequences is performed by the method developed by Sanger et al. [Proc. Natl. Acad. Sci. USA, 74 (1977) 5463–5467] using the kit distributed by Amersham.

For the hybridization experiments, the normal conditions of stringency are generally as follows: hybridization: 3×SCC in the presence of 5×Denhart's at 65° C.; washing: 0.5×SSC at 65° C.

1. Isolation of the 5HT5a receptor

Sequence comparisons between the different known serotonin receptors bring out some degree of conservation, especially in some potential transmembrane regions such as domains III and IV. With the aim of demonstrating and isolating a new receptor, three degenerate oligonucleotides corresponding to these two regions were prepared, and then used in a series of PCR reactions on a rat brain RNA preparation. The sequence of the degenerate oligonucleotides (i)–(iii) is given in the sequences SEQ ID No. 3–5.

The PCR reactions were carried out in the following manner: 5 μg of adult rat brain RNA were subjected to a reverse transcription reaction in the presence of 500 ng of oligonucleotide (i) and 200 units of MMLV reverse transcriptase (BRL). One half of the product of this reaction was then subjected to 30 amplification cycles in the presence of 5 units of Taq polymerase (Cetus) and 1 μg of oligonucleotide (i) and of oligonucleotide (ii). $\frac{1}{20}$ of the product of this reaction was then subjected to 30 additional amplification cycles in the presence of the oligonucleotides (i) and (iii). The products thereby obtained were digested with the enzymes BamHI and HindIII, inserted at the corresponding sites of the Bluescript plasmid (Stratagene) and sequenced. One of the fragments thereby obtained, displaying some degree of homology with the serotonin receptors, was labelled by "random priming" (Feinberg and Vogelstein, Analytical Biochemistry 132 (1984) 6), and used as probe to screen a rat brain cDNA library constructed in the phage UniZap (Stratagene). Among the positive phages obtained, one, designated NS and carried by plasmid pNS, contained a 4-kb insert. This phage was isolated, and its insert was then introduced into the Bluescript plasmid. The sequence of this fragment was determined over approximately 1.6 kb on both strands using the dideoxynucleotide technique, by means of synthetic oligonucleotides.

The sequence thereby obtained is presented in the sequence SEQ ID No. 1. It shows that the cDNA isolated carries an open reading frame of 357 amino acids. Moreover, hydrophobicity analysis shows that this protein carries seven hydrophobic domains, a distinctive feature encountered in members of the family of receptors coupled to G proteins. The N-terminal end contains, moreover, two N-glycosylation sites, and the presumed cytoplasmic domain contains the consensus sites of phosphorylation by protein kinases C and A.

2. Sequence homology study

The sequence of the 5HT5a receptor isolated above was compared with the sequences of the following receptors coupled to G proteins: 5HT1 B, 5HT1 D, 5HT1A, 5HT-dro2A, 5HT-dro1, α2, D2, β1, D1, H2, 5HT1C and 5HT2. These experiments revealed some degree of homology in the potential transmembrane domain and in some loops, but not in the terminal regions or in the third cytoplasmic loop. FIG. 1 gives the % homologies in the conserved regions.

As is apparent from this figure, the homology with the known receptors is low, the best result being obtained with the drosophila serotonin receptor HT-dro2A (37% homology).

3. Expression of the 5HT5a receptor in Cos-7 cells and pharmacological characterization The cDNA fragment isolated in Example 1 was inserted into a eukaryotic expression vector, which was used to transfect Cos-7 cells. The membranes of the transfected cells obtained were then prepared and tested for their capacity to bind some labelled serotonin ligands.

The 4-kb cDNA coding for the 5HT5a receptor was isolated from plasmid pNS in the form of an EcoRI-XhoI fragment, and then inserted at the corresponding sites of the vector p513. The vector p513 is derived from the vector pSG5 [Green et al., Nucl. Acids Res. 16 (1988) 369] by addition of a multicloning site. The recombinant vector thereby obtained, designated p513NS, was then used (20 μg per 10 cm dish) to transfect Cos-7 cells in the presence of calcium phosphate.

48 hours after transfection, the recombinant cells are harvested, and the membranes are prepared according to the technique described by Amlaiky and Caron [J.Biol. Chem. 260 (1985) 1983]. Saturation binding and competition experiments were then carried out on these membranes in the presence of the following radiolabelled ligands: [125I]-LSD, [$^{125}$I]-cyanopindolol, [$^3$H]-8-OH-DPAT and [$^3$H]-spiperone. For this purpose, membrane samples (10–20 μg of proteins) were incubated for 10 minutes at 37° C. in the presence of the ligand in a final volume of 250 μl of 50 mM Tris-HCl buffer (pH 7.4). The reaction is then stopped by filtration under vacuum on Whatman GF/C glass fibre filters and rinsing 4 times with 4 ml of 50 mM Tris-HCl buffer (pH 7.4). Non-specific binding was determined in the presence of 10 μM 5HT. Radioactivity was measured with a γ counter.

The results obtained show that, although [$^{125}$I]-cyanopindolol, [$^3$H]-8-OH-DPAT and [$^3$H]-spiperone do not bind to the membranes prepared, [$^{125}$I]-LSD possesses a saturable binding site with a Kd=340 pM and a Bmax=1.6 pmol/mg of membrane proteins (FIG. 2). In a control experiment, it was, moreover, shown that [$^{125}$I]-LSD did not bind Cos-7 cells transfected with plasmid p513.

To determine the pharmacological profile of this receptor, the [$^{125}$I]-LSD bound to the membranes was displaced in the presence of different serotonin drugs (Table 1). These different drugs show the following order of efficacy of displacement: 2-bromo-LSD>ergotamine>5-CT>methysergide>5HT=RU24969>bufotenine>yohimbine=8-OH-DPAT (Table 1). Ketanserin, (±)-pindolol, sumatriptan, dopamine and norepinephrine are inactive.

4. Expression of the 5HT5a receptor in NIH-3T3 cells and pharmocological study

The cDNA cloned in Example 1 was also expressed in NIH-3T3 cells, which do not endogenously express any serotonin receptor. For this purpose, the recombinant expression vector described in 3. above was used. It was introduced (20 μg per 10 cm dish) into NIH-3T3 cells by transfection in the presence of calcium phosphate, at the same time as the vector pRSVneo [Gorman et al., Science 221 (1983) 551], carrying the G418 resistance gene (1 μg per 10 cm plate). The transformant clones were selected in the presence of 0.5 mg of G418. The clones isolated were then amplified, and the total RNAs of these clones were prepared and analysed by Northern blotting for the expression of 5HT5a mRNA. 2 clones were selected in this way, NS1 and NS4, expressing high and low levels, respectively, of 5HT5a mRNA.

The membranes of the cells of these clones were then prepared and tested under the conditions described above for their capacity to bind some labelled serotonin ligands, and to determine the affinity of the receptors for the said ligands.

The results obtained show that the membranes of these 2 clones possess high-affinity binding sites for [$^{125}$I]-LSD, indicating that these 2 clones express 5HT5a receptors. A control experiment showed, in effect, that untransfected NIH-3T3 cells were incapable of binding [$^{125}$I]-LSD. Different displacement experiments were then carried out (Table 1). In the case of 5HT, 5CT, sumatriptan and 8-OH-DPAT, the competition curves obtained were biphasic, and an analysis of the results revealed 2 binding components, one with a high affinity and the other with a lower affinity.

5. Search for homologous sequences in other tissues

The nucleotide sequence SEQ ID No. 1 was then used to demonstrate homologous sequences on other tissues. For this purpose, three techniques were used:

Northern blot hybridization,

PCR in situ hybridization.

The tissues used to search for homologous sequences are the following ones of murine origin: brain, cerebellum, kidney, liver, spinal cord, spleen, lung and heart.

5.1. Search by Northern blot hybridization

Poly(A) mRNAs were prepared from the tissues mentioned above according to the technique described by Cathala et al. (DNA 2(4) (1983)), followed by passage through an oligo(dT)-cellulose column. These mRNAs were then fractionated on 1% agarose-formaldehyde gel and thereafter transferred onto nitrocellulose filters. The probe used for hybridization corresponds to the whole 4-kb EcoRI-XhoI fragment described in Example 1 (SEQ ID No. 1), previously labelled with $^{32}$P by "random priming". Hybridization was carried out under highly stringent conditions: 42° C. in 20 mM sodium phosphate buffer (pH 6.5) containing 50% of formamide, 5×SSC, 1 Denhardt's, 0.1% of SDS and 100 μg/ml of tRNA. Washes were performed at 60° C. in 0.1×SSC, 0.1% SDS buffer.

Figures 3A, 3B:
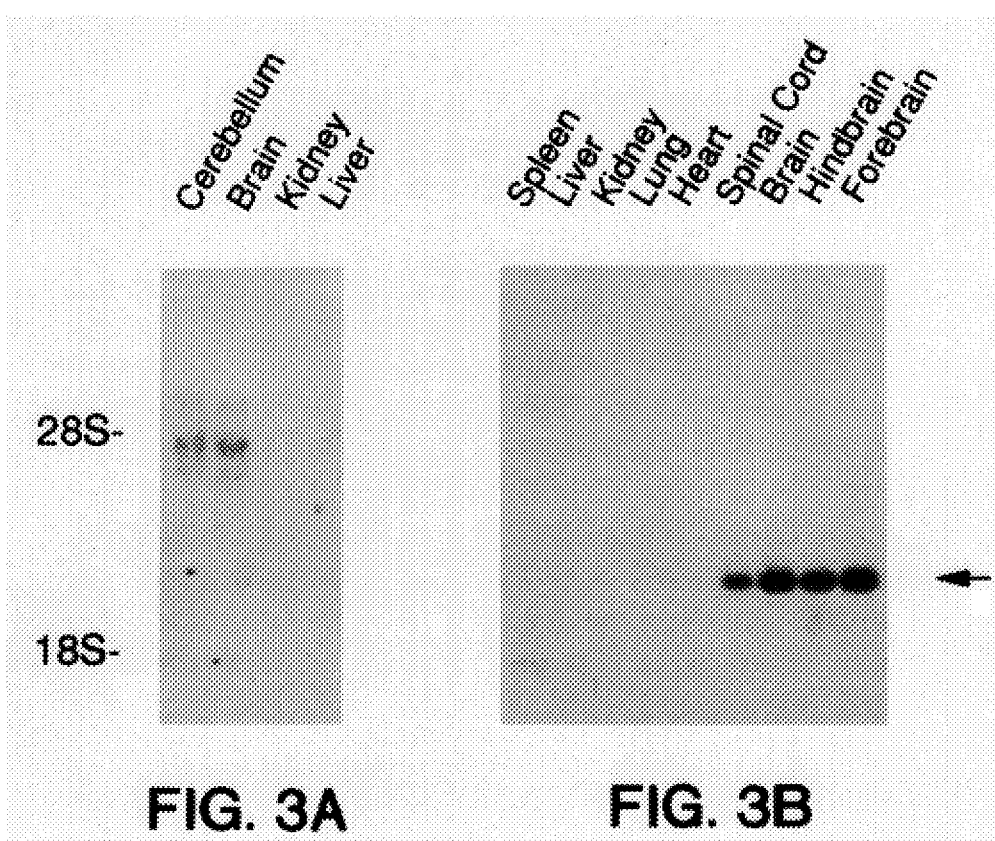

This study enabled three homologous transcripts, of 5.8 kb, 5 kb and 4.5 kb, to be demonstrated in the brain and the cerebellum (FIG. 3a).

5.2. Search by PCR

To search by PCR, the probes (iv) SEQ ID No. 6 and (v) SEQ ID No. 7 were used

The probe (iv) corresponds to position 1351 on the sequence SEQ ID No. 1, and the probe (v) to position 947.

Total RNAs were prepared from the different tissues studied, using the technique described by Cathala et al. mentioned above. 1 μg of these RNAs was subjected to reverse transcription in the presence of 200 units of MMLV reverse transcriptase and 300 ng of the probe (iv) for 1 hour at 37° C. One half of the product of this reaction was then amplified (30 cycles) in the presence of 5 units of Taq polymerase (Cetus) and 500 ng of the probes (iv) and (v). An aliquot of this reaction was also sampled after 20 amplification cycles. The products thereby obtained were then transferred onto nitrocellulose filters and hybridized under the conditions described in 5.1. above.

This study enabled homologous specific DNA fragments to be demonstrated in the spinal cord and the brain (FIG. 3b).

5.3. Search by in situ hybridization

In situ hybridization experiments were carried out on cryostat sections of brain of adult rats (approximately 8 weeks old) according to the technique described by Hafen et al. [EMBO J. 2(1983) 617]. The probe used for these experiments is a single-stranded RNA obtained by transcription in the presence of T7 polymerase and [$^{35}$S]-CTP using plasmid pNS as template.

This study enabled homologous sequences according to the invention to be demonstrated in the cerebral cortex, the hippocampus and the granular layer of the cerebellum, and in the olfactory bulb.

6. Isolation of the human receptor

According to the methodology described in 5. above, the human 5HT5a receptor was cloned.

For this purpose, a human genomic DNA library was prepared from placenta, by partial digestion with the enzyme Mbo1, separation on salt gradients and subcloning into the vector lamda GEM 12 linearized with BamHI (host bacterium: TAP 90).

The library thereby obtained was then screened by means of the probe described in Example 5.1. The DNA fragments which hybridize with this probe were isolated, subcloned into a Bluescript plasmid, amplified and then sequenced in both directions according to the dideoxynucleotide technique. Amplification was carried out by the PCR technique: 20 cycles in the presence of *Thermus aquaticus* polymerase (2.5 units; Cetus), oligonucleotides 1 (SEQ ID No. 10) and 2 (SEQ ID No. 11) for part A of the receptor upstream of the intron, and oligonucleotides 3 (SEQ ID No. 12) and 4 (SEQ ID No. 13) for part B of the receptor downstream of the intron. The fragment A was digested with the enzymes NotI and XhoI, and the fragment B with the enzymes EcoRI and XhoI. These fragments were subcloned into an expression vector P514.

The sequence obtained is presented in the sequence SEQ ID No. 8.

It is understood that the same experiments may be repeated using other tissues, in particular tissues of human origin, and other probes. Moreover, the homologous sequences demonstrated in these experiments can then obviously be isolated and/or amplified by standard techniques of molecular biology.

TABLE 1

|  | pKi | | | | |
| --- | --- | --- | --- | --- | --- |
|  | 5HT5 (Cos-7) | 5HT5 (NIH-3T3) low | 5HT5 (NIH-3T3) high | 5HT1D (rat cortex) | 5HT1D (Calf caudate) |
| 5-HT | 6.6 (7) | 6.2 (2) | 8.0 (2) | 8.7 | 8.4 |
| 5-CT | 7.8 (3) | 7.9 (2) | 9.5 (2) | 8.6 | 8.6 |
| RU24969 | 6.5 (2) | | | | 7.3 |
| TFMPP | 5.6 (2) | | | 6.6 | 6.2 |
| 8-OH-DPAT | 5.9 (2) | 5.7 (2) | 7.0 (2) | 6.6 | 5.9 |
| Sumatriptan | 4.8 (2) | 5.2 (2) | 7.8 (2) | | 7.5 |
| Bufotenine | 6.0 (2) | | | | 8.1 |
| Methysergide | 7.2 (5) | 7.1 (2) | | 7.3 | 8.4 |
| Ergotamine | 8.4 (2) | | | | 7.8 |
| 2-Bromo LSD | 8.7 (2) | | | | |
| Yohimbine | 6.0 (2) | | | | 7.1 |
| (±)Pindolol | 4.7 (2) | | | <5 | 5.2 |
| (-)Propanolol | 4.9 (2) | | | | 5.5 |
| Ketanserin | 4.8 (2) | | | <5 | 5.7 |
| Spiperone | 5.6 (2) | | | | 5.3 |
| Dopamine | 4.1 (2) | | | | |
| (-)Norepinephrine | 2.8 (2) | | | | |

We claim:

1. An isolated polypeptide comprising the peptide sequence SEQ ID No. 2 or SEQ ID No. 9.

2. An isolated nucleotide sequence coding for a polypeptide according to claim 1, or the complementary strand of said nucleotide sequence.

3. A nucleotide sequence according to claim 1, wherein said sequence is selected from the group consisting of genomic, cDNA RNA, synthetic and semi-synthetic sequences.

4. A nucleotide sequence according to claim 3, comprising sequence SEQ ID No. 1, SEQ ID No. 8 or their complementary strands.

5. A nucleotide sequence according to claim 2, wherein said sequence coding for the said polypeptide is operably linked to signals permitting expression of said nucleotide sequence in a cell host.

6. A recombinant cell comprising a nucleotide sequence according to claim 2.

7. A recombinant cell according to claim 6, selected from the group consisting of eukaryotic cells and prokaryotic cells.

8. A method of producing a polypeptide according to claim 1 comprising culturing a host cell comprising a nucleotide sequence encoding said polypeptide under conditions permitting expression of said nucleotide sequence.

9. A nucleotide probe selected from the group consisting of the sequences SEQ ID No.6, 7, 10, 11, 12, and 13.

10. A method for demonstrating and/or isolating ligands of the polypeptides as defined in claim 1 comprising:

contacting a molecule or a mixture containing different molecules with a recombinant eukaryotic cell expressing at its surface a polypeptide as defined in claim 1, under conditions permitting interaction between the said polypeptide and the said molecule, and detection and/or isolation of the molecules bound to the said polypeptide.

11. A method for demonstrating and/or isolating modulators of the polypeptides as defined in claim 1 comprising:

contacting a molecule or a mixture containing different molecules with a recombinant eukaryotic cell expressing at its surface a polypeptide as defined in claim 1, in the presence of 5HT, under conditions permitting interaction between the said polypeptide and 5HT, and detection and/or isolation of molecules capable of modulating the activity of 5HT with respect to the said polypeptide.

12. An isolated 5HT5A serotonin receptor, wherein said receptor binds serotonin and has the pharmacological profile-for displacement of [125I]-LSD of 2-bromo-LSD>ergotamine>5-CT>methysergide>5HT=RU24969>bufotenine>yohimbine=8-OH-DPAT, and wherein Ketanserin, (±)-pindolol, sumatriptan, dopamine and norepinephrine are inactive.

13. An isolated nucleotide sequence coding for a serotonin receptor according to claim 12 or the complementary strand of said nucleotide sequence.

14. A recombinant cell comprising a nucleotide sequence according to claim 13.

15. A method of producing a polypeptide according to claim 12 comprising culturing a host cell comprising a nucleotide sequence encoding said polypeptide under conditions permitting expression of said nucleotide sequence.

\* \* \* \* \*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1686 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 509..1582

( x i ) SEQUENCE DESCRIPTION: SEQ ID NO:1:

```
GGCACGAGGC  CGTCTCCAGA  AAGCAGGTAT  CTACGTGGCT  TCCAGTCCCC  AACCCCACC          60

CCTCGGAGCC  ACTGCCGGGA  GAGGGGGGAG  GTGGGCAAGG  AGCAACCCTG  GACCAGCGAC        120

TGTTCTGACG  CACTAGCTGA  GTTCTGGGCA  TCCACCCTGC  ACTGGGCGGG  GGCGACCCAA        180

GGATGCTCTG  CTGCAGGCGA  CCAGACAACA  GTCTCCGCCT  AGGTGAGGAA  CAGCAAGGCA        240

TGTGATAGCA  AAAGGCGGGC  CCTGGCTTCT  AGATTCAGCC  CCTTGAGTCC  GCTTTCCATA        300

TCTCTAAGGA  TACCTGGGCT  GTGCTGCTTG  TAGCCCAGCA  CCCTCCTCTC  TGCTACAATT        360

TCCTCCGGAC  TCTGACTGGG  TGGAGACTGA  GGCCAGGTTC  TTGGCTCTTA  GCAAAATCCT        420

CTCCATTGGC  CATCGGTCGC  AAACATCTAG  ATTGACTTCA  GTGGGCTCGG  TGGCAACACA        480

GTCTAAACAC  AGGTGTCCTG  GGACAGCA  ATG GAT CTG CCT GTA AAC TTG ACC            532
                                Met Asp Leu Pro Val Asn Leu Thr
                                  1               5
```

-continued

| | | | | | | | | | | | | | | | |
|---|---|---|---|---|---|---|---|---|---|---|---|---|---|---|---|
| TCC | TTT | TCT | CTC | TCT | ACT | CCC | TCC | TCT | TTG | GAA | CCT | AAC | CGC | AGC | TTG | 580 |
| Ser | Phe | Ser | Leu | Ser | Thr | Pro | Ser | Ser | Leu | Glu | Pro | Asn | Arg | Ser | Leu |
|  | 10 |  |  |  | 15 |  |  |  |  | 20 |  |  |  |  |  |
| GAC | ACG | GAA | GTC | CTG | CGC | CCT | AGT | CGG | CCT | TTT | CTC | TCA | GCT | TTC | CGA | 628 |
| Asp | Thr | Glu | Val | Leu | Arg | Pro | Ser | Arg | Pro | Phe | Leu | Ser | Ala | Phe | Arg |
| 25 |  |  |  | 30 |  |  |  |  | 35 |  |  |  |  |  | 40 |
| GTG | CTA | GTC | CTG | ACT | TTG | TTG | GGC | TTT | CTA | GCT | GCG | GCC | ACA | TTC | ACT | 676 |
| Val | Leu | Val | Leu | Thr | Leu | Leu | Gly | Phe | Leu | Ala | Ala | Ala | Thr | Phe | Thr |
|  |  |  |  | 45 |  |  |  |  | 50 |  |  |  |  | 55 |  |
| TGG | AAC | CTG | CTG | GTG | CTG | GCT | ACC | ATC | CTC | AAG | GTA | CGC | ACC | TTC | CAC | 724 |
| Trp | Asn | Leu | Leu | Val | Leu | Ala | Thr | Ile | Leu | Lys | Val | Arg | Thr | Phe | His |
|  |  | 60 |  |  |  |  | 65 |  |  |  |  | 70 |  |  |  |
| CGA | GTA | CCA | CAC | AAC | CTG | GTA | GCT | TCC | ATG | GCC | ATC | TCG | GAT | GTG | CTA | 772 |
| Arg | Val | Pro | His | Asn | Leu | Val | Ala | Ser | Met | Ala | Ile | Ser | Asp | Val | Leu |
|  |  | 75 |  |  |  |  | 80 |  |  |  |  | 85 |  |  |  |
| GTG | GCT | GTG | CTG | GTT | ATG | CCA | CTG | AGC | CTG | GTA | CAT | GAG | CTG | TCT | GGG | 820 |
| Val | Ala | Val | Leu | Val | Met | Pro | Leu | Ser | Leu | Val | His | Glu | Leu | Ser | Gly |
|  | 90 |  |  |  | 95 |  |  |  |  | 100 |  |  |  |  |  |
| CGC | CGC | TGG | CAG | CTG | GGC | CGG | CGT | CTA | TGC | CAG | CTG | TGG | ATC | GCA | TGT | 868 |
| Arg | Arg | Trp | Gln | Leu | Gly | Arg | Arg | Leu | Cys | Gln | Leu | Trp | Ile | Ala | Cys |
| 105 |  |  |  | 110 |  |  |  |  | 115 |  |  |  |  |  | 120 |
| GAC | GTG | CTC | TGC | TGT | ACT | GCC | AGC | ATC | TGG | AAT | GTG | ACA | GCA | ATA | GCA | 916 |
| Asp | Val | Leu | Cys | Cys | Thr | Ala | Ser | Ile | Trp | Asn | Val | Thr | Ala | Ile | Ala |
|  |  |  |  | 125 |  |  |  |  | 130 |  |  |  |  | 135 |  |
| CTG | GAC | CGC | TAC | TGG | TCA | ATC | ACG | CGC | CAC | CTG | GAG | TAC | ACA | CTC | CGT | 964 |
| Leu | Asp | Arg | Tyr | Trp | Ser | Ile | Thr | Arg | His | Leu | Glu | Tyr | Thr | Leu | Arg |
|  |  |  | 140 |  |  |  |  | 145 |  |  |  |  | 150 |  |  |
| ACC | CGC | AAG | CGT | GTC | TCC | AAT | GTG | ATG | ATC | CTG | CTC | ACC | TGG | GCA | CTC | 1012 |
| Thr | Arg | Lys | Arg | Val | Ser | Asn | Val | Met | Ile | Leu | Leu | Thr | Trp | Ala | Leu |
|  |  | 155 |  |  |  |  | 160 |  |  |  |  | 165 |  |  |  |
| TCC | ACT | GTC | ATC | TCT | CTG | GCT | CCA | CTG | CTA | TTT | GGC | TGG | GGA | GAG | ACT | 1060 |
| Ser | Thr | Val | Ile | Ser | Leu | Ala | Pro | Leu | Leu | Phe | Gly | Trp | Gly | Glu | Thr |
|  | 170 |  |  |  |  | 175 |  |  |  |  | 180 |  |  |  |  |
| TAT | TCT | GAG | CCC | AGT | GAG | GAA | TGC | CAA | GTC | AGT | CGC | GAG | CCT | TCC | TAC | 1108 |
| Tyr | Ser | Glu | Pro | Ser | Glu | Glu | Cys | Gln | Val | Ser | Arg | Glu | Pro | Ser | Tyr |
| 185 |  |  |  |  | 190 |  |  |  |  | 195 |  |  |  |  | 200 |
| ACC | GTG | TTC | TCC | ACC | GTG | GGT | GCC | TTC | TAC | CTG | CCG | CTG | TGG | CTG | GTG | 1156 |
| Thr | Val | Phe | Ser | Thr | Val | Gly | Ala | Phe | Tyr | Leu | Pro | Leu | Trp | Leu | Val |
|  |  |  |  | 205 |  |  |  |  | 210 |  |  |  |  | 215 |  |
| CTC | TTT | GTG | TAC | TGG | AAA | ATT | TAC | AGG | GCG | GCG | AAA | TTC | CGC | ATG | GGC | 1204 |
| Leu | Phe | Val | Tyr | Trp | Lys | Ile | Tyr | Arg | Ala | Ala | Lys | Phe | Arg | Met | Gly |
|  |  |  | 220 |  |  |  |  | 225 |  |  |  |  | 230 |  |  |
| TCC | AGG | AAG | ACT | AAC | AGC | GTC | TCC | CCC | GTA | CCC | GAA | GCT | GTG | GAG | GTG | 1252 |
| Ser | Arg | Lys | Thr | Asn | Ser | Val | Ser | Pro | Val | Pro | Glu | Ala | Val | Glu | Val |
|  |  | 235 |  |  |  |  | 240 |  |  |  |  | 245 |  |  |  |
| AAG | AAT | GCT | ACA | CAA | CAT | CCC | CAG | ATG | GTG | TTC | ACG | GCC | CGC | CAT | GCC | 1300 |
| Lys | Asn | Ala | Thr | Gln | His | Pro | Gln | Met | Val | Phe | Thr | Ala | Arg | His | Ala |
|  | 250 |  |  |  |  | 255 |  |  |  |  | 260 |  |  |  |  |
| ACC | GTC | ACC | TTC | CAG | ACA | GAA | GGG | GAT | ACG | TGG | AGG | GAG | CAG | AAG | GAG | 1348 |
| Thr | Val | Thr | Phe | Gln | Thr | Glu | Gly | Asp | Thr | Trp | Arg | Glu | Gln | Lys | Glu |
| 265 |  |  |  |  | 270 |  |  |  |  | 275 |  |  |  |  | 280 |
| CAA | AGG | GCA | GCC | CTC | ATG | GTG | GGC | ATC | CTC | ATC | GGA | GTG | TTT | GTG | CTC | 1396 |
| Gln | Arg | Ala | Ala | Leu | Met | Val | Gly | Ile | Leu | Ile | Gly | Val | Phe | Val | Leu |
|  |  |  |  | 285 |  |  |  |  | 290 |  |  |  |  | 295 |  |
| TGC | TGG | TTC | CCT | TTC | TTC | GTC | ACA | GAG | CTC | ATC | AGT | CCC | CTG | TGT | TCC | 1444 |
| Cys | Trp | Phe | Pro | Phe | Phe | Val | Thr | Glu | Leu | Ile | Ser | Pro | Leu | Cys | Ser |
|  |  |  | 300 |  |  |  |  | 305 |  |  |  |  | 310 |  |  |
| TGG | GAC | GTC | CCT | GCC | ATC | TGG | AAG | AGC | ATC | TTC | CTG | TGG | TTG | GGC | TAT | 1492 |
| Trp | Asp | Val | Pro | Ala | Ile | Trp | Lys | Ser | Ile | Phe | Leu | Trp | Leu | Gly | Tyr |
|  |  | 315 |  |  |  |  | 320 |  |  |  |  | 325 |  |  |  |

-continued

```
TCT  AAT  TCC  TTC  TTC  AAC  CCA  CTC  ATC  TAC  ACA  GCA  TTC  AAC  AGG  AGC        1540
Ser  Asn  Ser  Phe  Phe  Asn  Pro  Leu  Ile  Tyr  Thr  Ala  Phe  Asn  Arg  Ser
     330                      335                      340

TAC  AGC  AGT  GCT  TTC  AAG  GTC  TTC  TTC  TCC  AAG  CAA  CAA  TGAGAGACCA           1589
Tyr  Ser  Ser  Ala  Phe  Lys  Val  Phe  Phe  Ser  Lys  Gln  Gln
345                      350                      355

CATGGGAGTG  CCTTCTTCCC  ATAGCTTGTA  GCTCAGTGGG  TTATATTGTC  CCATGAACCT                1649

TTGCAGGCTG  CCCAGCTGTC  TTTGAGGACA  AGATCCA                                            1686
```

( 2 ) INFORMATION FOR SEQ ID NO:2:

( i ) SEQUENCE CHARACTERISTICS:
        ( A ) LENGTH: 357 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Leu  Pro  Val  Asn  Leu  Thr  Ser  Phe  Ser  Leu  Ser  Thr  Pro  Ser
 1                  5                    10                      15

Ser  Leu  Glu  Pro  Asn  Arg  Ser  Leu  Asp  Thr  Glu  Val  Leu  Arg  Pro  Ser
               20                    25                      30

Arg  Pro  Phe  Leu  Ser  Ala  Phe  Arg  Val  Leu  Val  Leu  Thr  Leu  Leu  Gly
                35                     40                     45

Phe  Leu  Ala  Ala  Ala  Thr  Phe  Thr  Trp  Asn  Leu  Leu  Val  Leu  Ala  Thr
     50                      55                           60

Ile  Leu  Lys  Val  Arg  Thr  Phe  His  Arg  Val  Pro  His  Asn  Leu  Val  Ala
 65                      70                     75                        80

Ser  Met  Ala  Ile  Ser  Asp  Val  Leu  Val  Ala  Val  Leu  Val  Met  Pro  Leu
                85                          90                     95

Ser  Leu  Val  His  Glu  Leu  Ser  Gly  Arg  Arg  Trp  Gln  Leu  Gly  Arg  Arg
               100                    105                     110

Leu  Cys  Gln  Leu  Trp  Ile  Ala  Cys  Asp  Val  Leu  Cys  Cys  Thr  Ala  Ser
               115                    120                     125

Ile  Trp  Asn  Val  Thr  Ala  Ile  Ala  Leu  Asp  Arg  Tyr  Trp  Ser  Ile  Thr
     130                      135                     140

Arg  His  Leu  Glu  Tyr  Thr  Leu  Arg  Thr  Arg  Lys  Arg  Val  Ser  Asn  Val
145                      150                     155                       160

Met  Ile  Leu  Leu  Thr  Trp  Ala  Leu  Ser  Thr  Val  Ile  Ser  Leu  Ala  Pro
                    165                     170                     175

Leu  Leu  Phe  Gly  Trp  Gly  Glu  Thr  Tyr  Ser  Glu  Pro  Ser  Glu  Glu  Cys
               180                     185                     190

Gln  Val  Ser  Arg  Glu  Pro  Ser  Tyr  Thr  Val  Phe  Ser  Thr  Val  Gly  Ala
               195                     200                     205

Phe  Tyr  Leu  Pro  Leu  Trp  Leu  Val  Leu  Phe  Val  Tyr  Trp  Lys  Ile  Tyr
     210                      215                     220

Arg  Ala  Ala  Lys  Phe  Arg  Met  Gly  Ser  Arg  Lys  Thr  Asn  Ser  Val  Ser
225                      230                     235                       240

Pro  Val  Pro  Glu  Ala  Val  Glu  Val  Lys  Asn  Ala  Thr  Gln  His  Pro  Gln
               245                     250                     255

Met  Val  Phe  Thr  Ala  Arg  His  Ala  Thr  Val  Thr  Phe  Gln  Thr  Glu  Gly
               260                     265                     270

Asp  Thr  Trp  Arg  Glu  Gln  Lys  Glu  Gln  Arg  Ala  Ala  Leu  Met  Val  Gly
               275                     280                     285

Ile  Leu  Ile  Gly  Val  Phe  Val  Leu  Cys  Trp  Phe  Pro  Phe  Phe  Val  Thr
```

|  |  |  |  |  | 290 |  |  |  |  | 295 |  |  |  |  | 300 |  |  |  |  |
|---|---|---|---|---|---|---|---|---|---|---|---|---|---|---|---|---|---|---|---|
| Glu | Leu | Ile | Ser | Pro | Leu | Cys | Ser | Trp | Asp | Val | Pro | Ala | Ile | Trp | Lys |
| 305 |  |  |  |  | 310 |  |  |  |  | 315 |  |  |  |  | 320 |
| Ser | Ile | Phe | Leu | Trp | Leu | Gly | Tyr | Ser | Asn | Ser | Phe | Phe | Asn | Pro | Leu |
|  |  |  |  | 325 |  |  |  |  | 330 |  |  |  |  | 335 |  |
| Ile | Tyr | Thr | Ala | Phe | Asn | Arg | Ser | Tyr | Ser | Ser | Ala | Phe | Lys | Val | Phe |
|  |  |  | 340 |  |  |  |  | 345 |  |  |  |  | 350 |  |  |
| Phe | Ser | Lys | Gln | Gln |
|  |  | 355 |  |  |

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:3:

AGAACTAGTG GATCCAARAA NGGNARCCAR CA        32

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:4:

CTTGATATCG AATTCGAYRT NCTNTGYTGY AC        32

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:5:

GGTATCGATA AGCTTATHGC YCTNGAYMGN TA        32

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:6:

CTTCTGCTCC CTCCACGTAT C                                                                                      21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:7:

CGCCACCTGG AGTACACACT C                                                                                      21

( 2 ) INFORMATION FOR SEQ ID NO:8:

( i ) SEQUENCE CHARACTERISTICS:
        ( A ) LENGTH: 1073 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 1..1071

( x i ) SEQUENCE DESCRIPTION: SEQ ID NO:8:

```
ATG GAT TTA CCT GTG AAC CTA ACC TCC TTT TCC CTC TCC ACC CCC TCC      48
Met Asp Leu Pro Val Asn Leu Thr Ser Phe Ser Leu Ser Thr Pro Ser
 1               5                  10                  15

CCT TTG GAG ACC AAC CAC AGC CTC GGC AAA GAC GAC CTG CGC CCC AGC      96
Pro Leu Glu Thr Asn His Ser Leu Gly Lys Asp Asp Leu Arg Pro Ser
             20                  25                  30

TCG CCC CTG CTC TNG GTC NTC GGA GTG CTT ATT CTC ACC TTG CTG GGC     144
Ser Pro Leu Leu Xaa Val Xaa Gly Val Leu Ile Leu Thr Leu Leu Gly
         35                  40                  45

TTT CTG GTG GCG GCG ACG TTC GCC TGG AAC CTG CTG GTG CTG GCG ACC     192
Phe Leu Val Ala Ala Thr Phe Ala Trp Asn Leu Leu Val Leu Ala Thr
     50                  55                  60

ATC CTC CGT GTA CGC ACC TTC CAC CGC GTG CCC CAC AAC CTG GTG GCA     240
Ile Leu Arg Val Arg Thr Phe His Arg Val Pro His Asn Leu Val Ala
 65                  70                  75                  80

TCC ATG GCC GTC TCG GAT GTC CTG GTG GCC GCG CTG GTC ATG CCG CTG     288
Ser Met Ala Val Ser Asp Val Leu Val Ala Ala Leu Val Met Pro Leu
                 85                  90                  95

AGC CTG GTG CAC GAG CTG TCC GGG CGC CGC TGG CAG CTA GGT CGG AGG     336
Ser Leu Val His Glu Leu Ser Gly Arg Arg Trp Gln Leu Gly Arg Arg
            100                 105                 110

CTG TGC CAG CTT TGG ATC GCG TGC GAC GTG CTT TGC TGC ACG GCC AGC     384
Leu Cys Gln Leu Trp Ile Ala Cys Asp Val Leu Cys Cys Thr Ala Ser
        115                 120                 125

ATC TGG AAC GTG ACG GCC ATA GCA CTG GAC CGC TAC TGG TCC ATC ACG     432
Ile Trp Asn Val Thr Ala Ile Ala Leu Asp Arg Tyr Trp Ser Ile Thr
    130                 135                 140

CGC CAC ATG GAA TAC ACG CTC CGC ACC CGC AAG TGC GTC TCC AAC GTC     480
Arg His Met Glu Tyr Thr Leu Arg Thr Arg Lys Cys Val Ser Asn Val
145                 150                 155                 160

ATG ATC GCG CTC ACC TGG GCA CTC NCC ACT GTC ATC TCT CTG GCC CCG     528
```

| | | | | | | | | | | | | | | | | |
|---|---|---|---|---|---|---|---|---|---|---|---|---|---|---|---|---|
| Met | Ile | Ala | Leu | Thr 165 | Trp | Ala | Leu | Xaa 170 | Thr | Val | Ile | Ser | Leu 175 | Ala | Pro | |
| CTG Leu | CTT Leu | TTT Phe | GGC Gly 180 | TGG Trp | GGA Gly | GAG Glu | ACG Thr | TAC Tyr 185 | TCT Ser | GAG Glu | GGC Gly | AGC Ser | GAG Glu 190 | GAG Glu | TGC Cys | 576 |
| CAG Gln | GTA Val | AGC Ser 195 | CGC Arg | GAG Glu | CCT Pro | TCC Ser | TAC Tyr | GCC Ala 200 | GTG Val | TTC Phe | TCC Ser | ACC Thr | GTA Val 205 | GGC Gly | GCC Ala | 624 |
| TTC Phe | TAC Tyr 210 | CTG Leu | CCG Pro | CTC Leu | TGT Cys | GTG Val 215 | GTG Val | CTC Leu | TTC Phe | GTG Val | TAC Tyr 220 | TGG Trp | AAG Lys | ATC Ile | TAC Tyr | 672 |
| AAG Lys 225 | GCT Ala | ACC Thr | AAG Lys | TTC Phe | CGC Arg 230 | GTG Val | GGC Gly | TCC Ser | AGG Arg | AAG Lys 235 | ACC Thr | AAT Asn | AGC Ser | GTC Val | TCA Ser 240 | 720 |
| CCC Pro | ATA Ile | TCC Ser | GAA Glu | GCT Ala 245 | GTG Val | GAG Glu | GTG Val | AAG Lys | GAC Asp 250 | TCT Ser | GCC Ala | CAA Gln | CAG Gln | CCC Pro 255 | CAG Gln | 768 |
| ATG Met | GTG Val | TTC Phe | ACG Thr 260 | GTC Val | CGC Arg | CAC His | GCC Ala | ACC Thr 265 | GTC Val | ACC Thr | TTC Phe | CAG Gln | CCA Pro 270 | GAA Glu | GGG Gly | 816 |
| GAC Asp | ACG Thr | TGT Cys 275 | CGG Arg | GAG Glu | CAG Gln | AAG Lys | GAG Glu 280 | CAG Gln | CGG Arg | CCC Pro | GCC Ala | CTC Leu 285 | ATG Met | GTG Val | GGC Gly | 864 |
| ATC Ile | CTC Leu 290 | ATT Ile | GGC Gly | GTG Val | TTC Phe | GTG Val 295 | CTC Leu | TGC Cys | TGG Trp | ATC Ile | CCC Pro 300 | TTC Phe | TTT Phe | CTC Leu | ACC Thr | 912 |
| GAG Glu 305 | CTC Leu | ATC Ile | AGT Ser | CCC Pro | CTC Leu 310 | TGC Cys | TCC Ser | TGT Cys | GAC Asp | ATC Ile 315 | CCC Pro | GCC Ala | ATC Ile | TGG Trp | AAA Lys 320 | 960 |
| AGC Ser | ATC Ile | TTC Phe | CTG Leu | TGG Trp 325 | CTT Leu | GGC Gly | TAC Tyr | TCC Ser | AAC Asn 330 | TCC Ser | TTC Phe | TTT Phe | AAC Asn | CCC Pro 335 | CTG Leu | 1008 |
| ATC Ile | TAT Tyr | ACG Thr | GCT Ala 340 | TTC Phe | AAC Asn | AAG Lys | AAC Asn | TAC Tyr 345 | AAC Asn | AGC Ser | GCC Ala | TTC Phe | AAG Lys 350 | AAC Asn | TTC Phe | 1056 |
| TTT Phe | TCT Ser | AGG Arg 355 | CAA Gln | CAC His | TG | | | | | | | | | | | 1073 |

( 2 ) INFORMATION FOR SEQ ID NO:9:

( i ) SEQUENCE CHARACTERISTICS:
        ( A ) LENGTH: 357 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | | |
|---|---|---|---|---|---|---|---|---|---|---|---|---|---|---|---|
| Met 1 | Asp | Leu | Pro | Val 5 | Asn | Leu | Thr | Ser | Phe 10 | Ser | Leu | Ser | Thr | Pro 15 | Ser |
| Pro | Leu | Glu | Thr 20 | Asn | His | Ser | Leu | Gly 25 | Lys | Asp | Asp | Leu | Arg 30 | Pro | Ser |
| Ser | Pro | Leu 35 | Leu | Xaa | Val | Xaa | Gly 40 | Val | Leu | Ile | Leu | Thr 45 | Leu | Leu | Gly |
| Phe | Leu 50 | Val | Ala | Ala | Thr | Phe 55 | Ala | Trp | Asn | Leu | Leu 60 | Val | Leu | Ala | Thr |
| Ile 65 | Leu | Arg | Val | Arg | Thr 70 | Phe | His | Arg | Val | Pro 75 | His | Asn | Leu | Val | Ala 80 |
| Ser | Met | Ala | Val | Ser 85 | Asp | Val | Leu | Val | Ala 90 | Ala | Leu | Val | Met | Pro 95 | Leu |

| Ser | Leu | Val | His | Glu | Leu | Ser | Gly | Arg | Arg | Trp | Gln | Leu | Gly | Arg | Arg |
|  |  |  | 100 |  |  |  | 105 |  |  |  |  | 110 |  |  |  |

| Leu | Cys | Gln | Leu | Trp | Ile | Ala | Cys | Asp | Val | Leu | Cys | Cys | Thr | Ala | Ser |
|  |  | 115 |  |  |  |  | 120 |  |  |  |  | 125 |  |  |  |

| Ile | Trp | Asn | Val | Thr | Ala | Ile | Ala | Leu | Asp | Arg | Tyr | Trp | Ser | Ile | Thr |
|  |  | 130 |  |  |  | 135 |  |  |  |  | 140 |  |  |  |  |

| Arg | His | Met | Glu | Tyr | Thr | Leu | Arg | Thr | Arg | Lys | Cys | Val | Ser | Asn | Val |
| 145 |  |  |  |  | 150 |  |  |  |  | 155 |  |  |  |  | 160 |

| Met | Ile | Ala | Leu | Thr | Trp | Ala | Leu | Xaa | Thr | Val | Ile | Ser | Leu | Ala | Pro |
|  |  |  |  | 165 |  |  |  | 170 |  |  |  |  |  | 175 |  |

| Leu | Leu | Phe | Gly | Trp | Gly | Glu | Thr | Tyr | Ser | Glu | Gly | Ser | Glu | Glu | Cys |
|  |  |  | 180 |  |  |  |  | 185 |  |  |  |  | 190 |  |  |

| Gln | Val | Ser | Arg | Glu | Pro | Ser | Tyr | Ala | Val | Phe | Ser | Thr | Val | Gly | Ala |
|  |  | 195 |  |  |  |  | 200 |  |  |  |  | 205 |  |  |  |

| Phe | Tyr | Leu | Pro | Leu | Cys | Val | Val | Leu | Phe | Val | Tyr | Trp | Lys | Ile | Tyr |
|  | 210 |  |  |  |  | 215 |  |  |  |  | 220 |  |  |  |  |

| Lys | Ala | Thr | Lys | Phe | Arg | Val | Gly | Ser | Arg | Lys | Thr | Asn | Ser | Val | Ser |
| 225 |  |  |  |  | 230 |  |  |  |  | 235 |  |  |  |  | 240 |

| Pro | Ile | Ser | Glu | Ala | Val | Glu | Val | Lys | Asp | Ser | Ala | Gln | Gln | Pro | Gln |
|  |  |  |  | 245 |  |  |  | 250 |  |  |  |  |  | 255 |  |

| Met | Val | Phe | Thr | Val | Arg | His | Ala | Thr | Val | Thr | Phe | Gln | Pro | Glu | Gly |
|  |  |  | 260 |  |  |  |  | 265 |  |  |  |  | 270 |  |  |

| Asp | Thr | Cys | Arg | Glu | Gln | Lys | Glu | Gln | Arg | Pro | Ala | Leu | Met | Val | Gly |
|  |  | 275 |  |  |  |  | 280 |  |  |  |  | 285 |  |  |  |

| Ile | Leu | Ile | Gly | Val | Phe | Val | Leu | Cys | Trp | Ile | Pro | Phe | Phe | Leu | Thr |
|  | 290 |  |  |  |  | 295 |  |  |  |  | 300 |  |  |  |  |

| Glu | Leu | Ile | Ser | Pro | Leu | Cys | Ser | Cys | Asp | Ile | Pro | Ala | Ile | Trp | Lys |
| 305 |  |  |  |  | 310 |  |  |  |  | 315 |  |  |  |  | 320 |

| Ser | Ile | Phe | Leu | Trp | Leu | Gly | Tyr | Ser | Asn | Ser | Phe | Phe | Asn | Pro | Leu |
|  |  |  |  | 325 |  |  |  |  | 330 |  |  |  |  | 335 |  |

| Ile | Tyr | Thr | Ala | Phe | Asn | Lys | Asn | Tyr | Asn | Ser | Ala | Phe | Lys | Asn | Phe |
|  |  |  | 340 |  |  |  |  | 345 |  |  |  |  | 350 |  |  |

| Phe | Ser | Arg | Gln | His |
|  |  | 355 |  |  |

( 2 ) INFORMATION FOR SEQ ID NO:10:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:10:

GCATGCGCGC  GGCCGCGGCA  CCATGGATTT  ACCTGTGAAC  CTA                4 3

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid -continued (iv) ANTI-SENSE: NO (xi) SEQUENCE DESCRIPTION: SEQ ID NO:11:

TTCGGATATC GGTGAGACGC                                                                       20

(2) INFORMATION FOR SEQ ID NO:12:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO:12:

CCGATATCCG AAGCTGTGGA GGTGAAGGAC TCTGCCCAAC A                                               41

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO:13:

AACCCGGGCT TAAGTCAGTG TTGCCTAGAA AAGAAGT                                                    37